US012478092B2

(12) United States Patent
Czarnotta et al.

(10) Patent No.: US 12,478,092 B2
(45) Date of Patent: Nov. 25, 2025

(54) METHOD AND DEVICE FOR EXAMINING ROD-SHAPED PRODUCTS OF THE CIGARETTE INDUSTRY

(71) Applicant: Focke & Co. (GmbH & Co. KG), Verden (DE)

(72) Inventors: Michael Czarnotta, Bremen (DE); Karl-Heinz Breithaupt, Dörverden (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 506 days.

(21) Appl. No.: 17/799,152

(22) PCT Filed: Feb. 17, 2021

(86) PCT No.: PCT/EP2021/053860
§ 371 (c)(1),
(2) Date: Aug. 11, 2022

(87) PCT Pub. No.: WO2021/165303
PCT Pub. Date: Aug. 26, 2021

(65) Prior Publication Data
US 2023/0073296 A1 Mar. 9, 2023

(30) Foreign Application Priority Data
Feb. 21, 2020 (DE) ........................ 102020001136.5

(51) Int. Cl.
*A24C 5/34* (2006.01)
*A24D 3/02* (2006.01)
(Continued)

(52) U.S. Cl.
CPC .......... *A24C 5/3412* (2013.01); *A24D 3/0216* (2013.01); *A24D 3/0295* (2013.01);
(Continued)

(58) Field of Classification Search
CPC .............................. A24C 5/3412; B65B 19/30
See application file for complete search history.

(56) References Cited

U.S. PATENT DOCUMENTS 3,818,223 A 6/1974 Gibson
4,307,963 A 12/1981 Bolt
(Continued)

FOREIGN PATENT DOCUMENTS

CN 102502000 A 6/2012
CN 202935608 U 5/2013
(Continued)

OTHER PUBLICATIONS

World Intellectual Property Organization, International Search Report (in a related application), May 21, 2021.
(Continued)

*Primary Examiner* — Eric Yaary
(74) *Attorney, Agent, or Firm* — Laurence P. Colton; Smith Tempel Blaha LLC

(57) ABSTRACT

A method and device for examining rod-shaped products of the cigarette industry, having a cylindrical lateral surface and two end faces formed by two filter elements arranged at opposite ends, the product having smokable material between the two end faces, by: a) irradiating the lateral surface using examination light whereby the examination light penetrates through the lateral surface at least partially into the product and at least partially exits again through one end face, the beams of which are incident on the lateral surface at an angle of at least 30° in relation to the longitudinal extension of the product; b) acquiring the examination light exiting the end face of the product using an electro-optical receiver, the main viewing direction of which is directed onto the end face; and c) evaluating the brightness
(Continued)

or light intensity of the examination light exiting the end face and acquired by the electro-optical receiver.

21 Claims, 6 Drawing Sheets

(51) Int. Cl.

| | |
|---|---|
| ***B65B 19/20*** | (2006.01) |
| ***B65B 19/30*** | (2006.01) |
| ***G01N 21/01*** | (2006.01) |
| ***G01N 21/47*** | (2006.01) |
| *G01N 33/00* | (2006.01) |

(52) U.S. Cl.

CPC .............. *B65B 19/20* (2013.01); *B65B 19/30* (2013.01); *G01N 21/01* (2013.01); *G01N 21/4738* (2013.01); *G01N 2021/4735* (2013.01); *G01N 33/0078* (2024.05)

(56) References Cited

U.S. PATENT DOCUMENTS

| | | | | |
|---|---|---|---|---|
| 4,941,482 A | 7/1990 | Heitmann | | |
| 5,596,187 A * | 1/1997 | Di Stefano | A24C 5/3412 | 250/222.1 |
| 6,437,317 B1 * | 8/2002 | Focke | A24C 5/3412 | 250/221 |
| 2017/0238599 A1 * | 8/2017 | Stanikowski | H04N 23/56 | |

FOREIGN PATENT DOCUMENTS

| | | | |
|---|---|---|---|
| DE | 2411231 | A1 | 9/1974 |
| DE | 2653298 | A1 | 6/1977 |
| DE | 3243204 | A1 | 5/1984 |
| DE | 3725366 | A1 | 2/1989 |
| DE | 19753333 | A1 | 6/1999 |
| DE | 19817824 | A1 | 10/1999 |
| DE | 10057329 | A1 | 5/2002 |
| DE | 102016013719 | A1 | 5/2018 |
| EP | 0553699 | A1 | 8/1993 |

OTHER PUBLICATIONS

Deutsches Patent—Und Markenamt (German Patent and Trademark Office), Recherchebericht (search in a related application), Oct. 28, 2020.

China National Intellectual Property Administration, Notification of the First Office Action (in a corresponding application), Jul. 30, 2025.

* cited by examiner

METHOD AND DEVICE FOR EXAMINING ROD-SHAPED PRODUCTS OF THE CIGARETTE INDUSTRY

CROSS REFERENCE TO RELATED APPLICATIONS

This application is the US national phase of and claims the benefit of and priority on International Application No. PCT/EP2021/053860 having an international filing date of 17 Feb. 2021, which claims priority on and the benefit of German Patent Application No. 10 2020 001 136.5 having a filing date of 21 Feb. 2020.

BACKGROUND OF THE INVENTION

Technical Field

The present invention relates to a method for examining rod-shaped products of the cigarette industry, in particular tobacco sticks, each having an in particular cylindrical lateral surface and two end faces, which are arranged at opposite ends, are formed in particular by two filter elements preferably of different lengths, and are in particular visually identical, wherein the rod-shaped product has smokable material, in particular tobacco, between the two end faces, preferably in a section arranged off-center. Furthermore, the invention relates to a device for examining such products.

Prior Art

Diverse examination methods for cigarettes or other rod-shaped products are known in the tobacco or cigarette industry, which are regularly used in the context of the packaging process of such products. In such a packaging process, the rod-shaped products are often combined to form separate product groups having one or more product layers, in which the cigarettes lie adjacent to one another and are aligned in a specific and identical manner. Conventional cigarettes are generally aligned in such a product group so that their end faces formed by the filter ends together form a first product group side and their end faces formed by the tobacco ends form an opposing second product group side. The product groups are then integrated into the respective package, for example, in a conventional cigarette package. In this context, it is necessary, inter alia, to recognize whether individual cigarettes are incorrectly arranged rotated by 180° in a product group, thus, for example, whether the filter end of a cigarette in the product group is incorrectly assigned to the product group side which is formed by the tobacco ends of the cigarettes. For this purpose, for example, recording an image of the filter ends of the cigarettes of a product group using a camera and identifying an incorrectly present tobacco end therein by means of image recognition technologies is known.

However, this method fails if the two ends of the rod-shaped products are visually indistinguishable from one another or are only distinguishable inadequately. This can be the case, for example, with novel products of the cigarette industry, such as tobacco sticks ("heat not burn"), of which embodiments are known in which both ends are formed by filters, the end faces of which are visually identical.

It would be conceivable in such a case to provide the lateral surfaces of the respective rod-shaped products with off-center imprints, to acquire the lateral surfaces and thus the imprints by means of cameras, and in this way recognize incorrect orientations of individual rod-shaped products in a product group, since in such a case the respective imprint would appear at an incorrect or unexpected position in the recorded image. However, this method would be complex since all rod-shaped products would have to be provided with the imprint. Moreover, it would no longer be applicable without errors in product groups having three or more product layers, since the middle product layers are covered by the outer product layers and thus cannot be examined using cameras.

BRIEF SUMMARY OF THE INVENTION

Proceeding therefrom, it is the object of the present invention to refine the method mentioned at the outset and the device mentioned at the outset. In particular in such a way that rod-shaped products having ends or end faces which are optically indistinguishable or are only distinguishable inadequately can also be reliably examined.

This object is achieved by a method and device having the features of the respective independent claims.

Accordingly, a method for examining the rod-shaped products of the cigarette industry mentioned at the outset is provided having the following measures:

a) irradiating the lateral surface of at least one rod-shaped product to be examined using examination light in such a way that the examination light penetrates through the lateral surface at least partially into the rod-shaped product and exits again at least partially through an end face, in particular using examination light, the beams of which are incident on the lateral surface at an angle of at least 30°, preferably at least 60°, particularly preferably 90° in relation to the longitudinal extension of the rod-shaped product,
b) acquiring the examination light exiting from the end face of the rod-shaped product to be examined using an electro-optical receiver for the examination light, which is assigned to the end face and the main viewing direction of which is directed on the end face, in particular a camera, and
c) evaluating the examination light exiting from the end face and acquired by the electro-optical receiver, in particular with regard to its brightness and/or light intensity.

It has been shown that the above-mentioned optical examination method enables an identification of the orientation of rod-shaped products in many cases even if the end faces are visually identical, for example, if both ends have filter elements, for example, as in the case of tobacco sticks for electrical tobacco heaters (heat not burn). In particular if the section of smokable material is arranged off-center in the rod-shaped product due to different lengths of the two filter elements, for example, thus is not arranged symmetrically in relation to the center plane of the rod-shaped product extending perpendicularly to the longitudinal axis, this results in a light absorption (for the examination light) along the longitudinal axis of the rod-shaped product, thus from one end face to the other end face, which is different depending on direction. This directional dependence of the absorption can then be utilized according to the invention. However, such a direction-dependent absorption is also theoretically conceivable in the case of two filter elements of equal length and central location of the section of smokable material. For example, if an additional absorbing element is contained in this section, in particular off-center, such as a flavor capsule or the like.

It is obvious that the method according to the invention can also be used in the case of conventional cigarettes having one tobacco end and one filter end.

Rod-shaped products of the cigarette industry in the scope of the application can accordingly in principle be conventional rod-shaped products having smokable material, such as cigarettes, cigarillos, or the like, but also alternative rod-shaped products having smokable material, such as tobacco sticks for electrical tobacco producers (with or without flavor capsule) or the like.

Insofar as in one preferred embodiment of the invention, one or more rod-shaped products each having a section of smokable material arranged off-center can be examined, the respective lateral surface of the respective rod-shaped product can be irradiated using examination beams of the examination light in such a way that the examination beams, after the penetration into the lateral surface on their way to the electro-optical receiver, in a first orientation of the respective rod-shaped product do not penetrate or would not penetrate any smokable material or a shorter section of smokable material inside the rod-shaped product, while they—with unchanged examination light or with spatially unchanged beam path of the examination light incident on the lateral surface—in a second orientation of the respective rod-shaped product opposite by 180°, penetrate or would penetrate smokable material or a longer section of smokable material within the rod-shaped product. Different light intensities accordingly result therefrom at the receiver in each case depending on the orientation of the rod-shaped product due to different absorptions of the examination beams, from which the actual orientation of the respective rod-shaped product can be ascertained.

Preferably, the brightness or light intensity of the acquired examination light can be compared to a reference value stored in a memory or to the brightness or light intensity of examination light exiting from the other end face at the opposite end of the same rod-shaped product or of examination light exiting from an end face of another rod-shaped product, the lateral surface of which is irradiated using examination light in such a way that the examination light penetrates at least partially through the lateral surface into the rod-shaped product and at least partially exits again through the end face, and the examination light of which exiting from the end face is acquired and evaluated using a or the electro-optical receiver.

According to the invention, an entire product group or product formation made up of rod-shaped products can preferably be examined, which has one or more product layers of rod-shaped products each arranged adjacent to one another in a row, the end faces of which each form one of two opposite product group sides at their opposite ends.

The lateral surface of each rod-shaped product of one or the product layer of the product group, preferably one or both outer product layers, can be irradiated using the examination light, wherein the examination light which exits from the end faces of the rod-shaped products of at least one of the two opposite product group sides is received and evaluated by a or the electro-optical receiver assigned to these end faces.

In particular a separate electro-optical receiver for acquiring the respective exiting examination light can be assigned to each of the opposite end faces of the rod-shaped product or the rod-shaped products, wherein examination light exiting from the one and also the other of the opposite end faces and acquired by the respective assigned electro-optical receiver is evaluated.

With regard to the (respective) assigned electro-optical receiver, its main viewing direction can thus extend perpendicularly to the end face(s) of the rod-shaped product or the rod-shaped products.

The or the respective assigned electro-optical receiver can preferably be designed as a camera, in particular as a CCD or CMOS camera, wherein the or the respective camera in particular records a common actual image of the one or more end face(s), and wherein the or the respective actual image is then evaluated.

In the context of the evaluation of the actual image, the brightness or light intensity of an end face depicted therein of a rod-shaped product can be compared to a stored reference value. Alternatively, in the context of the evaluation of the actual image, the brightness or light intensity of an end face depicted therein can be compared to the respective brightness or light intensity of at least one other end face depicted therein of a rod-shaped product of the same product layer or another product layer.

Each of the end faces at the two ends of the rod-shaped product or each rod-shaped product of one or the product group can respectively be assigned in particular a separate electro-optical receiver designed as a camera for acquiring the respective exiting examination light. In particular, in such a way that the main viewing direction of the respective camera is perpendicular to the respective assigned end face, each camera records an actual image of that end face to which it is assigned, and these actual images are evaluated in that the brightness or light intensity of the end face of the one end of the rod-shaped product depicted in the one actual image is compared to the brightness or light intensity of the end face of the other end of the rod-shaped product depicted in the other actual image.

Preferably, an error signal can be generated according to the invention for the case in which, in the context of the comparison of the brightness of the one end face to the respective brightness or light intensity of the other end face, a difference is established between the brightness or light intensity values, which goes beyond a predetermined amount.

Examination light can be applied from two different directions, in particular from directions opposite by 180° to the or each lateral surface of the or the respective rod-shaped products.

Furthermore, it can be provided in the examination of a product group having multiple product layers that examination light is applied to each of the lateral surfaces of the rod-shaped products of two outer product layers of the product group (from different sides), wherein the examination light using which the one outer product layer is irradiated originates from a different direction than the examination light using which the other outer product layer is irradiated, in particular from directions opposite by 180°.

For the case in which one or more rod-shaped products each having a section arranged off-center of smokable material are examined, it can be provided that the respective lateral surface of the respective rod-shaped product is irradiated using examination beams of the examination light in such a way that the examination beams, after the penetration into the lateral surface, on their way to the electro-optical receiver, do not penetrate or would not penetrate any smokable material or a shorter section of smokable material within the rod-shaped product in a first orientation of the respective rod-shaped product, while they penetrate or would penetrate smokable material or a longer section of smokable material within the rod-shaped product in a second orientation of the respective rod-shaped product opposite by 180°.

A suitable device for examining the rod-shaped products, in particular for carrying out the above method, has at least one illumination unit, from which examination light originates, which is directed onto the lateral surface of at least one rod-shaped product to be examined, preferably in such a way that its beams are incident on the lateral surface at an angle of at least 30°, preferably of at least 60°, particularly preferably 90° in relation to the longitudinal extension of the rod-shaped product, wherein the examination light penetrates through the lateral surface at least partially into the rod-shaped product and exits again at least partially through the end face, at least one electro-optical receiver, which is arranged in such a way that its main viewing direction is directed onto the end face of the rod-shaped product for acquiring the examination light, so that the examination light exiting from the end face of the rod-shaped product is acquired, and an evaluation unit, using which the examination light received by the electro-optical receiver can be evaluated, in particular with regard to its brightness and/or light intensity, preferably in such a way as described above.

The examination light is preferably directed onto a product group made up of rod-shaped products, which has one or more product layers of rod-shaped products each arranged adjacent to one another in a row, the end faces of which each form one of two opposite product group sides at their opposite ends, wherein the illumination unit is then designed in such a way that the examination light can be applied to the lateral surfaces of the rod-shaped products of at least one or the product layer, in particular one or both outer product layers, while the product group is located in a receptacle of a conveyor, in particular in the pocket of a rotatable revolver.

Furthermore, an illumination unit can preferably be provided which applies examination light to the lateral surfaces of a first outer product layer of the product group from a first side or from a first direction and to the lateral surfaces of a second outer product layer of the product group from a second other side or from a second different direction.

For this purpose, the illumination unit can have at least two light sources, wherein examination light of the one light source irradiates the one outer product layer and examination light of the other light source irradiates the other outer product layer.

The illumination unit can have a light guiding unit having one or more light guiding elements, such as mirrors or optical fibers, which conduct the examination light originating from the one light source of the illumination unit onto the lateral surfaces of the rod-shaped products of the one outer product layer of the product group and conduct the examination light originating from the other light source onto the lateral surfaces of the rod-shaped products of the other outer product layer of the product group.

However, it is also conceivable that the examination light of the same light source of the illumination unit is conducted by the light guiding unit to both one and also the other outer product layer and is applied thereto (from different sides or from different directions).

The above-mentioned two light sources of the illumination light or at least two light guiding elements of the light guiding unit of the illumination unit can be arranged adjacent to different sides of the product group, in particular in such a way that examination light is applied to the lateral surfaces of the first or the second product layer from different directions, preferably opposite by 180°.

Each of the opposite end faces of the rod-shaped product or the rod-shaped products can moreover respectively be assigned in particular a separate electro-optical receiver for acquiring the respective exiting examination light, in particular in such a way that the main viewing direction of the respective electro-optical receiver is oriented perpendicularly to the respective assigned end faces.

Each product group side which is formed by the end faces of the opposite ends of the rod-shaped products can also be assigned a separate electro-optical receiver for acquiring the examination light respectively exiting from all end faces of the respective product group side, in particular in such a way that the main viewing direction of the respective electro-optical receiver is oriented perpendicularly to the end faces of the respective product group side.

BRIEF DESCRIPTION OF THE DRAWINGS

Further features of the present invention result from the appended claims, the following description of preferred exemplary embodiments, and the appended drawings.

In the figures.

DETAILED DESCRIPTION OF PREFERRED EMBODIMENTS

Figure 1:
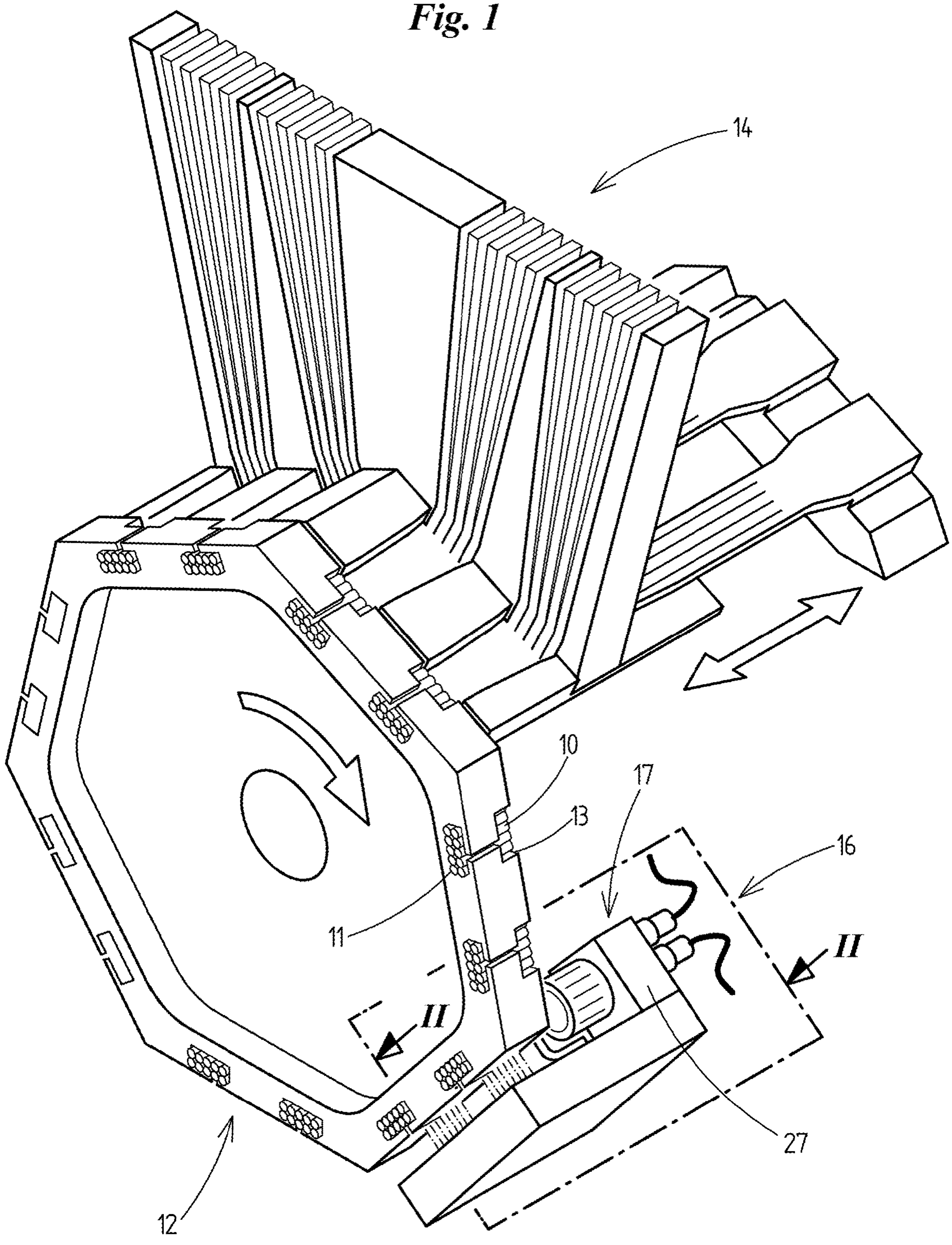
FIG. 1 shows a first embodiment of an examination device according to the invention for examining product groups of rod-shaped tobacco products, positioned in the region of a revolver for conveying the product groups, in perspective.

The examination method according to the invention and the examination device according to the invention is explained in the present case in conjunction with the examination of product groups 10 of rod-shaped products 11, namely tobacco sticks in the present case, which are conveyed in each of the exemplary embodiments of FIGS. 1-7 in receptacles 13 of a conveyor 12 moving by rotation, namely a revolver in the present case.

In the present case, the rod-shaped products 11 have an in particular cylindrical lateral surface 22 and at both ends end faces 23 and 24 extending transversely to the longitudinal extension of the respective rod-shaped product 11.

The end faces 23, 24 are formed by corresponding end faces of filter elements 20 or 21, respectively, known per se.

The end faces 23, 24 or the end faces of the filter elements 20, 21 correspondingly axially delimit the lateral surface 22 of the respective rod-shaped product 11.

A section 25 having smokable material 26 is located between the two filter elements 20, 21 or between the corresponding end faces 23, 24 of the respective rod-shaped product 11. The smokable material 26 can be, for example, classic tobacco or smokable liquids or the like.

This section 25 having smokable material 26 is arranged off-center or accordingly not symmetrical in relation to the center plane in the present case with respect to the center plane of the respective rod-shaped product 11 extending perpendicularly to the longitudinal axis of the rod-shaped product 11.

In the present case, the section 25 is arranged beyond the center plane of the rod-shaped product 11 completely in one half thereof, in particular adjacent to the filter element 21.

The filter elements 20, 21, between which the section 25 is arranged, have different lengths here.

Moreover, still further elements can be arranged between the filter elements 20, 21, in the present case shown as a filling part 19, for example.

The product groups 10 made of rod-shaped products 11 have multiple product layers 18 each made up of rod-shaped products 11 arranged adjacent to one another in a product layer 18. In the exemplary embodiments of FIGS. 1-6, these are each two product layers 18 each having five rod-shaped products 11. However, this can also be different.

Each product group 10 has product group sides formed by the rod-shaped products 11:

A first (front) product group side 28 is formed by the end faces 23 of the rod-shaped products 11 arranged in a common plane, a second opposite product group side 29 parallel to the first product group side 28 is formed by the end faces 24 at the respective other ends of the rod-shaped products 11 and are also arranged in a common plane.

A third (lower) and a fourth (upper) product group side 35 and 36, respectively, are formed or defined by the lateral surfaces 22 of the rod-shaped products 11.

With correct orientation of the rod-shaped products 11 in the corresponding product group 10, these are arranged or aligned in the product group 10 so that the respective identical filter elements 20 or 21 are each assigned to the same product group side 28 or 29, respectively.

The above-mentioned conveyor 12 is part of a packaging machine (not shown) known in the prior art for producing packages for product groups 10 of rod-shaped products 11 in each case as package content. Such packages can be, for example, hinge lid packages, but also any other types of packages, in which product groups of rod-shaped products 11 of the cigarette or tobacco industry can be packaged.

In the present case, the rod-shaped products 11 are supplied to the conveyor 12 from a magazine 14 to form the product groups 10, specifically by means of a pusher.

While the product groups 10 are located in the receptacles 13 of the conveyor 12, they are examined by an examination unit 16 in a way described in more detail hereinafter.

It is obvious that the illustrated examination unit 16 could also be arranged in various other regions of the packaging machine or the examination could also take place at other points of the packaging process.

Moreover, an individual examination of rod-shaped products 11 is theoretically also conceivable, without these having to be arranged within a product group 10 during the examination.

After the examination, the product groups 10 are conveyed for further handling to further assemblies of the packaging machine, which carry out the further measures known per se for packaging the rod-shaped products 11 or the product groups 10 in the corresponding packages, such as hinge lid packages or the like.

Figure 2:
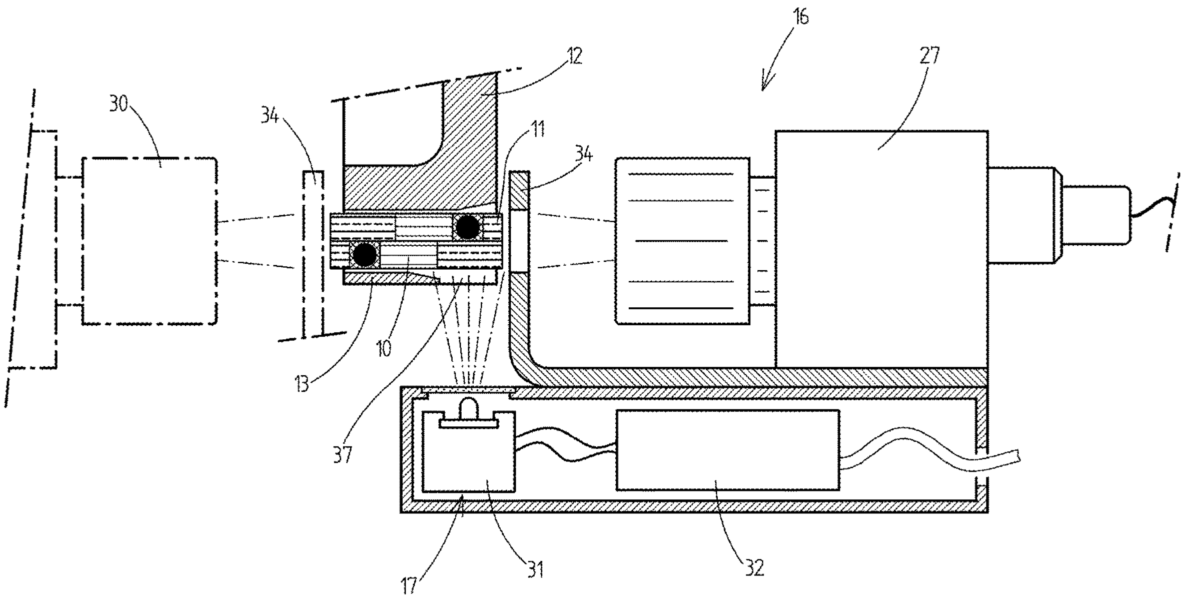
FIG. 2 shows a section along section plane II-II in FIG. 1.

In the present case, the conveyor 13—after the respective product groups 10 in the region of the magazine 14 have been inserted into the respective receptacle 13—is rotated further, so that in the present case two product groups 10 to be examined next are each conveyed into an examination position, cf. FIG. 2, in which they are examined by the examination unit 16.

For the examination in groups of the product groups 10 to be examined, which are located in the respective examination position, the examination unit 16 has two illumination units 17, namely one for each product group 10 to be examined, which each apply examination light to an assigned product group 10 located in the respective examination position.

In the present case, the illumination units 17 each have suitable light sources 13, in particular LEDs. These are each supplied with electric current by a supply unit 32.

The light sources 31 of the illumination units 17 in FIG. 2 are each arranged adjacent to the receptacles 13 of the conveyor 12 located in the respective examination position in such a way that the examination beams of the examination light are incident at an angle to the longitudinal axis or longitudinal extension of the rod-shaped products 11, thus not in parallel thereto, on the lateral surfaces 22 of the rod-shaped products 11 of the outer (arranged on the radial outside) product layer 18 of the product group 10, in the present case essentially perpendicularly or at an angle of 90° to the longitudinal extension of the rod-shaped products 11.

The light sources 31 of the illumination units 17 are each positioned for this purpose at a radial distance to the circumference of the conveyor 12 and provide a respective radial wall of the respective receptacle 13 with a (radial) opening 37, so that the lateral surfaces 22 of the rod-shaped products 11 of the outer product layer 18 can be irradiated using the examination light through the opening 37.

In addition to the illumination units 17, the examination device 16 has two electro-optical receivers 27 in the present case, preferably cameras. The electro-optical receivers 27 are each designed and oriented in such a way that their main viewing directions are each oriented on the end faces 23 of the corresponding product group sides 28 formed thereby of the respective product groups 10 to be examined, namely perpendicularly thereto in the present case.

Alternatively or additionally, moreover still further electro-optical receivers 30 can possibly be arranged on the opposite side of the conveyor 12 or the opposite product group side 29, the main viewing directions of which have each been directed accordingly on the end faces 24 of the opposite product group side 29, cf. FIG. 2.

Notwithstanding the illustration shown in FIG. 2, for example, the illumination units 17 could also be designed or arranged so that their examination light beams are not incident perpendicularly on the lateral surfaces 22 of the rod-shaped products 11, thus not at an angle of 90° relative to the lateral surfaces or to the longitudinal axis of the rod-shaped products 11, but rather at another, smaller angle, thus obliquely to the longitudinal axis.

In the examination process, the examination light of the illumination units 17 is conducted in the described manner onto the third (lower) product group side 35, namely onto the lateral surfaces 22 of the rod-shaped products 11 of the outer product layer 18.

The rod-shaped products 11 are predominantly irradiated using the examination light in the present case in the region of the (longer) filter elements 20, but this does not have to be the case.

The examination light penetrates into the rod-shaped products 11, radiates through them, is partially deflected in the interior, and then partially exits again via the end faces 23. This part exiting from the end faces 23 is acquired by the respective electro-optical receiver 27, which records a corresponding image, in which the end faces 23 are contained.

Another part of the examination light reaches the further or second product layer 18 (arranged farther radially inward), partially exits again through the end faces 23 of the rod-shaped products 11, and is also acquired by the respective or the same electro-optical receiver 27. The end faces 23 of the rod-shaped products 11 of this further, inner product layer 18 are preferably contained in the same image recording as the end faces 23 of the first, outer product layer 18.

To improve the acquisition of the end faces 23 or the examination light exiting from them, a screen 34 is moreover also arranged axially adjacent to the respective receptacle 13 of the conveyor 12 located in the examination position, by which the scattered light not originating from the end faces 23 is absorbed.

The detection of rod-shaped products 11 arranged in the non-correct orientation in the respective product group 10 will first be explained by way of example on the basis of FIGS. 3, 4*a*, and 4*b*.

Figure 3:
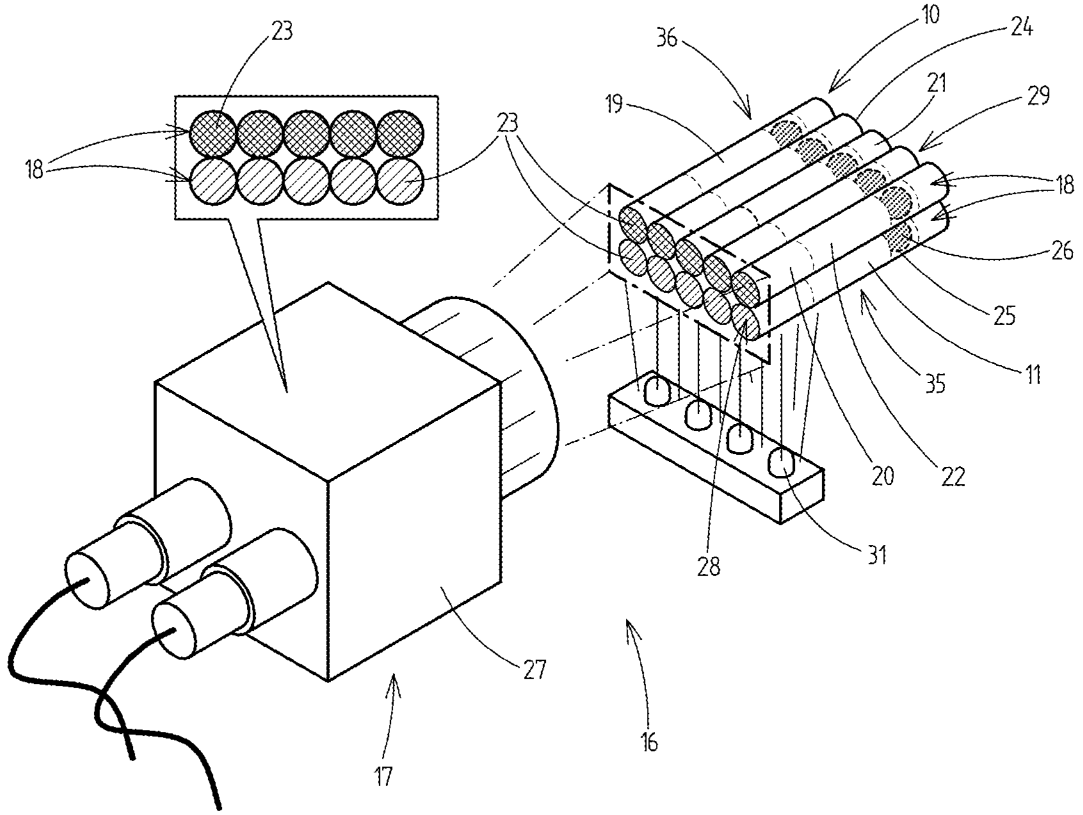
FIG. 3 shows components of the examination device from FIG. 1 in isolated illustration, in particular a camera which acquires a product group illuminated by an illumination unit, in perspective.

A product group 10 can be seen in FIG. 3, which exclusively has correctly oriented rod-shaped products 11. The rod-shaped products 11 of the product group 10 are arranged and oriented so that all (longer) filter elements 20 face toward the product group side 28 and the (shorter) filter elements 21 face toward the opposite product group side 29.

The respective electro-optical receiver 27 records an (electronic) image of the product group side 28 or all end faces 23. An evaluation unit (not shown), for example, a corresponding computer or a suitably equipped control unit, then evaluates the image in that, for example, the brightness or light intensity of the respective end faces 23 of the rod-shaped products 11 of a product layer 18 is ascertained in the image and compared either to stored reference value or to the ascertained brightness or light intensity values, respectively, of one or more other end faces 23 of rod-shaped products 11 of the same product layer 18.

In the context of this comparison, it is then recognized that all end faces 23 in FIG. 3 of the same product layer 18 each have the same or at least very similar brightness values, which is an indicator that all rod-shaped products 11 in the same product layer 18 are oriented in the same, correct manner.

Since only one or only the (lower) product group side 35 of the product group 10 is irradiated by the respective illumination unit 17, it can moreover be seen in the image of the end faces 23 that the end faces 23 of the outer product layer 18 appear brighter than the end faces 23 of the inner product layer 18, since the examination light is partially absorbed on its way to the inner product layer 18.

Figure 4A:
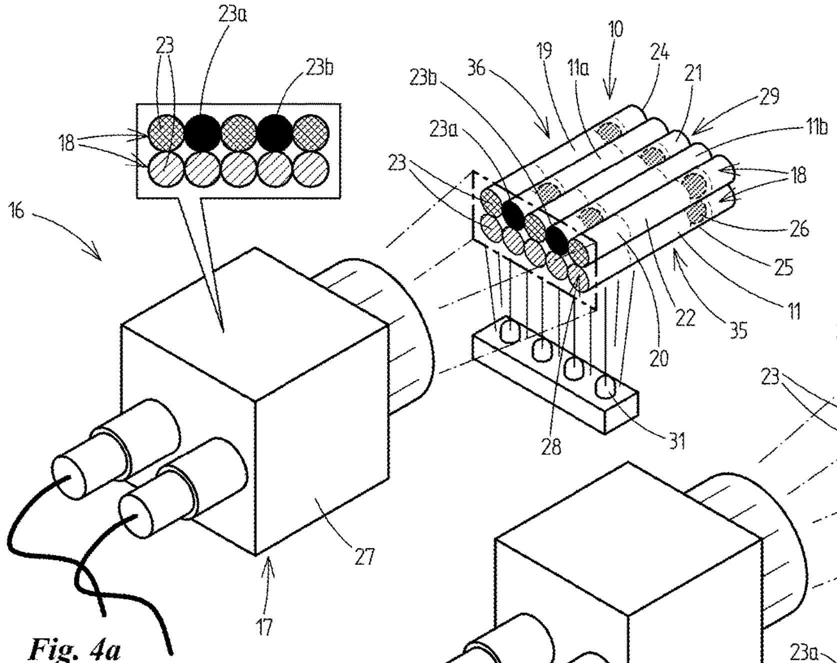
FIG. 4*a* shows an illustration similar to FIG. 3, wherein two rod-shaped products arranged in the same layer of the product group are arranged in incorrect orientation (rotated by 180°) in the product group.

A situation is shown in FIG. 4*a*, in which two incorrectly oriented rod-shaped products 11*a* and 11*b* are contained in the outer product layer 18.

In this case, the evaluation of the corresponding image results in a lower light intensity of the end faces 23*a* or 23*b* associated therewith. This is because due to the orientation rotated by 180° of the rod-shaped products 11*a* and 11*b*, the examination light, after it has entered the rod-shaped products 11*a* and 11*b*, is partially incident on the respective section 25 having the smokable material, where it is absorbed more strongly than in the region of the filter elements 20 or 21. This is because filter elements are generally made very light and have lower absorption values than smokable material such as tobacco.

This lower light intensity of the end faces 23*a* or 23*b*, either relative to reference values or in comparison to one or more of the other end faces 23 of the same product layer 18, is an indicator that the two rod-shaped products 11*a* and 11*b* are oriented the wrong way around.

An error signal can accordingly be generated and the corresponding product group 10 can be eliminated in the packaging process, for example.

Figure 4B:
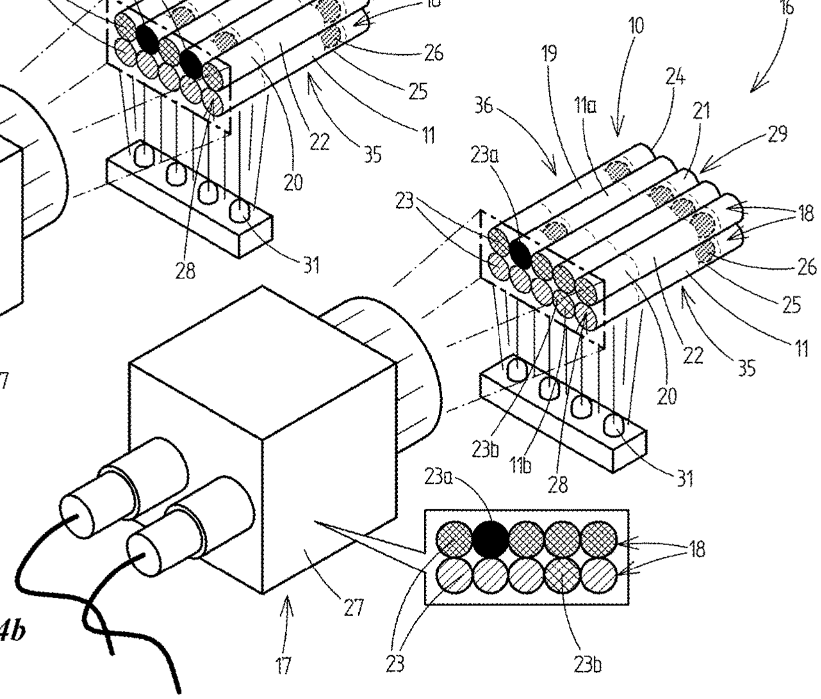
FIG. 4*b* shows an illustration similar to FIG. 3, wherein rod-shaped products are arranged in incorrect orientation in both layers of the product group.

In a similar manner, it can be seen on the basis of the corresponding recorded image in the example of FIG. 4*b* that in both product layers 18, an incorrectly oriented rod-shaped product 11*a* or 11*b* is arranged in the product group 11.

Figure 7:
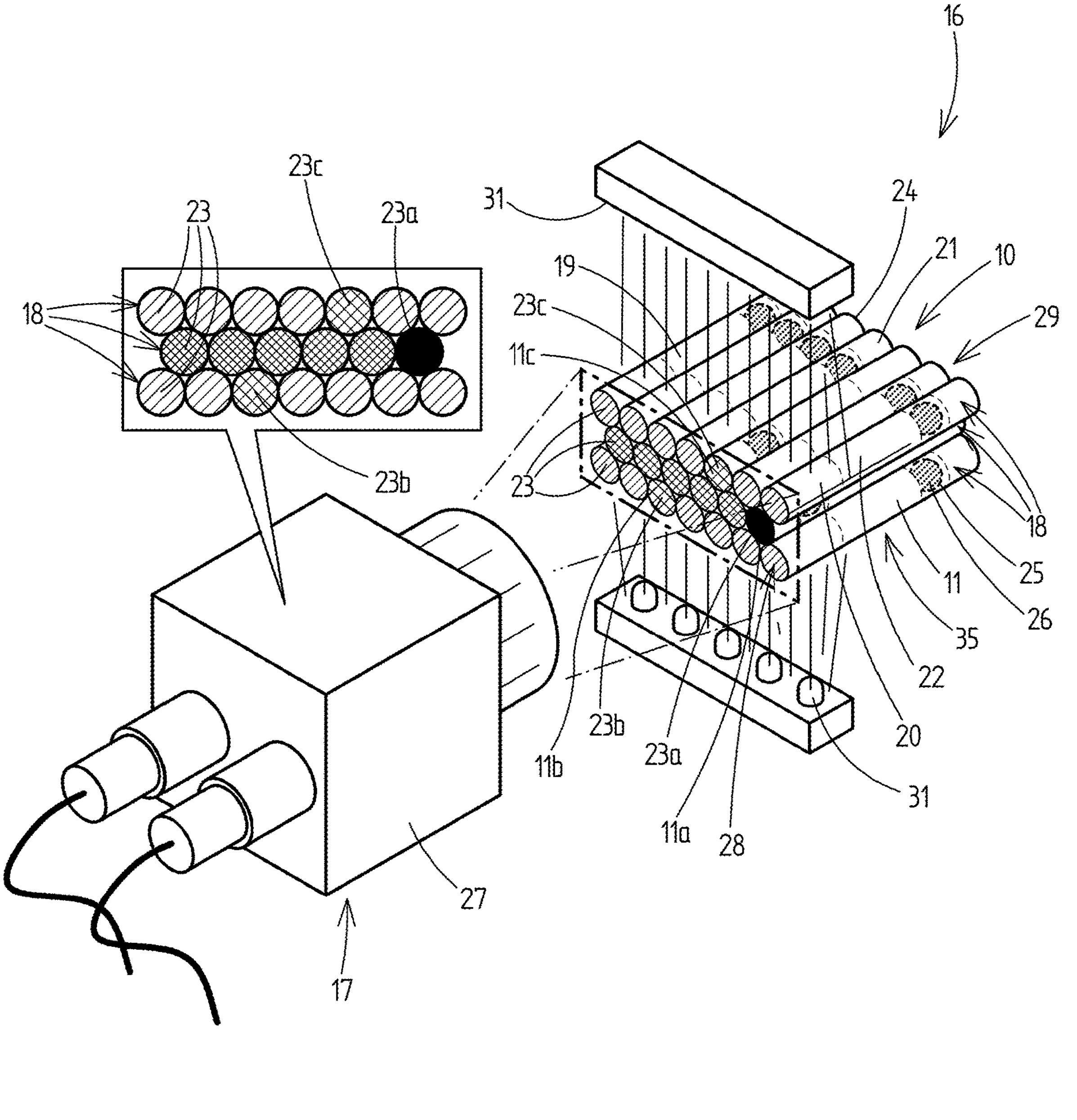
FIG. 7 shows a third alternative exemplary embodiment of an examination device according to the invention in an illustration similar to FIG. 3.

A variant is shown in FIG. 7 in which the product group 10 is formed not from two, but rather three product layers 18. In this case, irradiating the (upper) product group side 36 directly with examination light of the respective illumination unit 17 also suggests itself, since otherwise too little examination light would possibly penetrate into the upper product layer 18 or would arrive thereon, since the examination light first has to penetrate the lower and middle product layers 18 in FIG. 7.

Correspondingly, further light sources 31 of the illumination unit 17 are arranged directly adjacent to the (upper) product group side 36, which apply examination light directly to the upper product layer 18.

In the variant shown in FIG. 7—as can be seen on the end faces 23*a*, 23*b*, and 23*c*—three rod-shaped products 11*a*, 11*b*, and 11*c* are incorrectly oriented.

Figure 5:
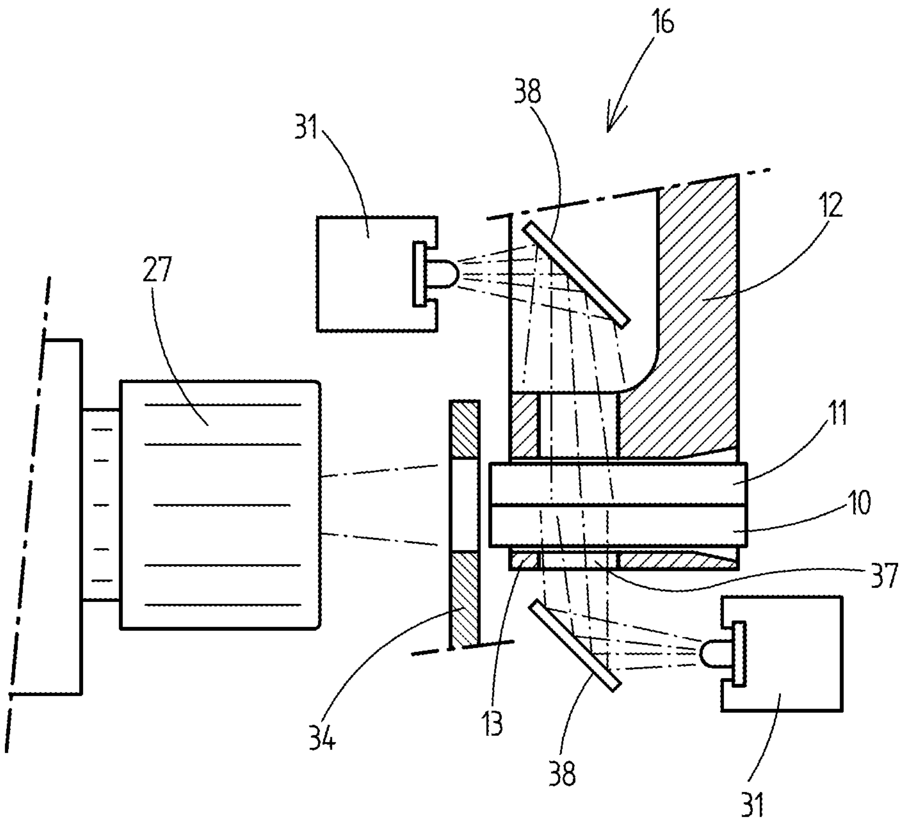
FIG. 5 shows a first alternative exemplary embodiment of an examination device according to the invention in a sectional illustration.

FIG. 5 shows that the examination light of the respective illumination unit 17, originating here from multiple light sources 31 arranged on different sides of the product group 10, but also via light guiding elements 38, in the present case mirrors (however, optical fibers can also be used, for example), of a light guiding unit can be conducted onto the product group 10. The light guiding elements 38 can then be arranged in a suitable manner adjacent to the conveyor 12, so that the examination light is incident in the above-described manner on the lateral surfaces 22 of the respective rod-shaped products 10 of the corresponding product layer 18.

Figure 6:
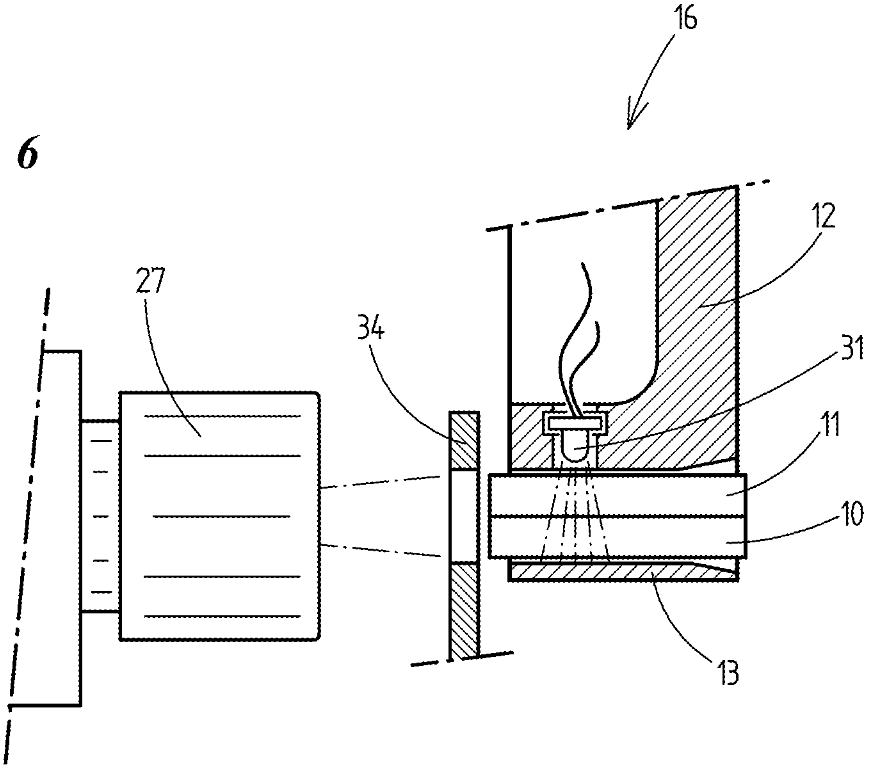
FIG. 6 shows a second alternative exemplary embodiment of an examination device according to the invention in a sectional illustration.

FIG. 6 shows that the one or more light sources 31 can also be integrated directly into the conveyor 12, so that the examination light can also be applied directly to the product group 10 (without light guiding unit).

With regard to the examination light in general, which is generated using the illumination unit(s) 17, it is thus conceivable that it can possibly also be applied in a punctiform manner to each of the individual rod-shaped products 11, for example, by means of individual laser beams.

LIST OF REFERENCE SIGNS

10 product group
11 rod-shaped product
11*a* rod-shaped product
11*b* rod-shaped product
11*c* rod-shaped product
12 conveyor
13 receptacle
14 magazine
16 examination unit

17 illumination unit
18 product layer
19 filling part
20 filter element
21 filter element
22 lateral surface
23 end face
23*a* end face
23*b* end face
23*c* end face
24 end face
25 section
26 smokable material
27 electro-optical receiver
28 front product group side
29 rear product group side
30 electro-optical receiver
31 light source
32 supply unit
34 screen
35 lower product group side
36 upper product group side
37 opening
38 light guiding element

The invention claimed is:

1. A method for examining rod-shaped products (11) of the cigarette industry, each having a cylindrical lateral surface (22) and two end faces (23, 24), which are arranged at opposite ends, wherein the rod-shaped product (11) has smokable material, between the two end faces (23, 24), comprising the steps of:

a) irradiating the lateral surface (22) of at least one rod-shaped product (11) of a product group (10) made of the rod-shaped products (11) to be examined, wherein the product group (10) has two or more product layers (16) of the rod-shaped products (11) each arranged adjacent to one another in a row, the end faces (23, 24) of which each form one of two opposite product group sides at their opposite ends, using examination light in such a way that the examination light penetrates through the lateral surface (22) at least partially into the rod-shaped product (11) and at least partially exits again through one end face (23, 24);

b) acquiring the examination light exiting from the end face (23, 24) of the rod-shaped product (11) to be examined using an electro-optical receiver for the examination light assigned to the end face (23, 24), the main viewing direction of which is directed onto the end face (23, 24); and c) evaluating the examination light exiting from the end face (23, 24) and acquired by the electro-optical receiver.

2. The method as claimed in claim 1, wherein the brightness or light intensity of the acquired examination light is compared to a reference value stored in a memory or to the brightness or light intensity of examination light exiting from the other end face (23, 24) at the opposite end of the same rod-shaped product (11) or of examination light exiting from an end face (23, 24) of another rod-shaped product (11), the lateral surface (22) of which is irradiated using examination light in such a way that the examination light penetrates through the lateral surface (22) at least partially into the rod-shaped product (11) and at least partially exits again through the end face (23, 24), and the examination light of which exiting from the end face (23, 24) is acquired and evaluated using an or the electro-optical receiver.

3. The method as claimed in claim 1, wherein the lateral surface (22) of each rod-shaped product (11) of one or the product layer (18) of the product group (10) is irradiated using examination light, and that the examination light which exits from the end faces (23, 24) of the rod-shaped products (11) from at least one of the two opposite product group sides is received and evaluated by an or the electro-optical receiver assigned to these end faces (23, 24).

4. The method as claimed in claim 1, wherein each of the opposite end faces (23, 24) of the rod-shaped product (11) or the rod-shaped products (11) is respectively assigned a separate electro-optical receiver for acquiring the respective exiting examination light, and that the examination light exiting from the one and also from the other of the opposite end faces (23, 24) and acquired by the respective assigned electro-optical receiver is evaluated.

5. The method as claimed in claim 1, wherein the main viewing direction of the or each assigned electro-optical receiver extends perpendicularly to the end face(s) (23, 24) of the rod-shaped product (11) or the rod-shaped products (11).

6. The method as claimed in claim 1, wherein the or the respective assigned electro-optical receiver is designed as a camera that the or the respective camera records an actual image of the one or more end face(s) (23, 24), and that the or the respective actual image is evaluated.

7. The method as claimed in claim 6, wherein, in the scope of the evaluation of the actual image, the brightness or light intensity of an end face (23, 24) of a rod-shaped product (1) depicted therein is compared to a stored reference value, or that in the scope of the evaluation of the actual image, the brightness or light intensity of an end face (23, 24) depicted therein is compared to the respective brightness or light intensity of at least one other end face (23, 24) of a rod-shaped product (11) depicted therein of the same product layer (18) or another product layer (18).

8. The method as claimed in claim 6, wherein each of the end faces (23, 24) at the two ends of the rod-shaped products (11) is respectively assigned a separate electro-optical receiver, designed as a camera, for acquiring the respective exiting examination light, that each camera respectively records an actual image of that end face (23, 24) to which it is assigned, and that these actual images are evaluated in that the brightness or light intensity of the end face (23, 24) of the one end of the rod-shaped product (11) depicted in the one actual image is compared to the brightness or light intensity of the end face (23, 24) of the other end of the rod-shaped product (11) depicted in the other actual image.

9. The method as claimed in claim 7, wherein an error signal is generated for the case that in the context of the comparison of the brightness of the one end face (23, 24) to the respective brightness or light intensity of the other end face (23, 24), a difference between the brightness or light intensity values is established which goes beyond a predetermined amount.

10. The method as claimed in claim 1, wherein examination light is applied to the lateral surface (22) of the or the respective rod-shaped product (11) from two different directions, or that examination light is applied (from different sides) to each of the lateral surfaces (22) of the rod-shaped products (11) of two outer product layers (18) of the product group (10), wherein the examination light, using which the one outer product layer (18) is irradiated, originates from a different direction than the examination light using which the other outer product layer (18) is irradiated.

11. The method as claimed in claim 1, wherein for the case that one or more rod-shaped products (11) each having a section of smokable material are examined, the respective lateral surface (22) of the respective rod-shaped product (11) is irradiated using examination beams of the examination light in such a way that the examination beams, after the penetration into the lateral surface (22), on their way to the electro-optical receiver in a first orientation of the respective rod-shaped product (11), do not penetrate or would not penetrate any smokable material or a shorter section of smokable material inside the rod-shaped product (11), while in a second orientation of the respective rod-shaped product (11) opposite by 180°, they penetrate or would penetrate smokable material or a longer section of smokable material inside the rod-shaped product (11).

12. The method as claimed in claim 1, wherein the two end faces (23, 24) are formed by two filter elements and/or are visually identical.

13. The method as claimed in claim 12, wherein the two filter elements are of different lengths.

14. The method as claimed in claim 1, wherein the smokable material is tobacco and/or arranged in an off-center section.

15. The method as claimed in claim 1, wherein the beams of the examination light are incident on the lateral surface (22) at an angle of at least 30° in relation to the longitudinal extension of the rod-shaped product (11).

16. The method as claimed in claim 1, wherein the examining light is acquired by using a camera as an electro-optical receiver and is evaluated with regard to its brightness or light intensity.

17. The method as claimed in claim 1, wherein the examination light acquired by the electro-optical receiver is evaluated with regard to its brightness or light intensity.

18. The method as claimed in claim 3, wherein the lateral surface (22) of each rod-shaped product (11) of one or both outer product layers (18) is irradiated using examination light.

19. The method as claimed in claim 6, wherein the or the respective assigned electro-optical receiver is designed as a CCD or CMOS camera.

20. The method as claimed in claim 8, wherein the main viewing direction of the respective camera is oriented perpendicularly to the respective assigned end face (23, 24).

21. The method as claimed in claim 11, wherein one or more rod-shaped products (11) each having a section of smokable material which is arranged off-center are examined.

* * * * *